United States Patent [19]

Olsen

[11] Patent Number: 4,508,823

[45] Date of Patent: * Apr. 2, 1985

[54] GENE SPLICING METHOD AND PRODUCTS PRODUCED THEREFROM

[75] Inventor: Ronald H. Olsen, Ann Arbor, Mich.

[73] Assignee: Microlife Technics, Inc., Sarasota, Fla.

[*] Notice: The portion of the term of this patent subsequent to Feb. 15, 2000 has been disclaimed.

[21] Appl. No.: 328,957

[22] Filed: Dec. 9, 1981

Related U.S. Application Data

[63] Continuation-in-part of Ser. No. 147,563, May 8, 1980, Pat. No. 4,374,200.

[51] Int. Cl.$^3$ .................. C12N 15/00; C12N 1/20; C12N 1/00; C12P 21/00; C12P 19/34; C12R 1/38; C12R 1/385

[52] U.S. Cl. .................. 435/172.3; 435/68; 435/91; 435/253; 435/317; 435/874; 435/875; 435/23; 435/29; 435/56; 435/72; 435/80

[58] Field of Search .............. 435/172, 68, 70, 91, 435/253, 317, 874, 875, 172.3; 536/27

[56] References Cited

U.S. PATENT DOCUMENTS

| | | | |
|---|---|---|---|
| 3,813,316 | 5/1974 | Chakrabarty | 435/248 |
| 4,237,224 | 12/1980 | Cohen et al. | 435/68 |
| 4,278,765 | 7/1981 | Debabov et al. | 435/172.3 |
| 4,374,200 | 2/1983 | Olsen | 435/172.3 |
| 4,376,164 | 3/1983 | Olsen | 435/317 |
| 4,418,194 | 11/1983 | Olsen | 435/68 |

OTHER PUBLICATIONS

Freifekder: *Molecular Biology*, Science Books International, 1983, pp. 107–108.
Wensink et al: Cell 3, 315, (1974).
Helling et al: in *Genetic Engineering*, Chakrabarty (ed.), CRC Press, 1978, pp. 1–30.
Macrina, F. D. Kepecko, K. Jones, D. Ayers and S. McCowen Plasmid 14:7–420, (1978).
Hansen, J. and R. Olsen, J. Bacteriol. 135:227–238, (1978).
Royle, Matsumoto and Holloway, J. Bacteriol. 145:145–155, (1981).
Bolivar, R., et al. Gene 2:95–113, (1977).
Bagdasarian et al, in: *Plasmids of Medical, Environmental and Commercial Importance*, Timmis et al. (Ed.), Elsevierl North-Holland, 1979, pp. 411–422.
Wood et al., J. Bacteriol. 145: 1448–1451, (1981).
Ditta et al: Proc. Natl. Acad. Sci. USA 77:7347–7351, (1980).
Guerry, LeBlanc and Falkow, J. Bacteriol. 116:1064–1066, (1973).
Mercer and Loutit, J. Bacteriol. 140:37–42, (1979).
Carbon, J. et al, Recombinant Molecules: Impact on Science and Society, Raven Press, New York, (1977), pp. 355–378.
Clarke, L., and J. Carbon, Proc. Nat. Acad. Sci. USA 72: 4361–4365, (1975).

*Primary Examiner*—Thomas G. Wiseman
*Assistant Examiner*—James Martinell
*Attorney, Agent, or Firm*—Ian C. McLeod

[57] ABSTRACT

An improved gene splicing and recombinant plasmid transformation method is described. The method includes mechanical fragmenting of chromosomal DNA followed by conventional digestion with a restriction enzyme and gene splicing into a vector to provide recombinant plasmids in a bank of at least about 100 different plasmids. The plasmids in the bank are provided for transformation into a suitable host, particularly a plasmid free bacterium of the same species from which the chromosomal DNA or the vector is derived. The method provides high transformation frequencies because of the presence of multiple "super coiled" or closed coiled recombinant plasmids in the bank. The method also allows for the direct selection of many different phenotypic traits in a pool of the transformed hosts. The selected hosts are useful for the production of various gene products.

16 Claims, 7 Drawing Figures

GENE SPLICING METHOD AND PRODUCTS PRODUCED THEREFROM

CROSS-REFERENCE TO RELATED APPLICATION

This application is a continuation-in-part of my pending application Ser. No. 147,563, filed May 8, 1980, U.S. Pat. No. 4,374,200.

BACKGROUND OF THE INVENTION

1. Field of the Invention

The present invention relates to an improved gene splicing method, to recombinant plasmids and to transformed hosts produced therefrom. In particular, the present invention relates to a method whereby the selection of transformed hosts having a particular phenotypic trait is greatly simplified.

2. Prior Art

The basic prior art is described in U.S. Pat. No. 4,237,224 to Cohen and Boyer. The pioneering effort described in this patent provided the starting point for the present invention and is familiar to all those skilled in the art. There is a large body of prior art which is directly related to this patent. The patent terminology is generally used herein.

In my U.S. patent application Ser. No. 147,563 and related foreign applications, I described new plasmid vectors derived from plasmid pRO 1600. These plasmid vectors are used in the present invention. U.S. Pat. No. 4,278,765 to Debabov et al describes other vectors and recombinant plasmids. U.S. Pat. No. 3,813,316 to Chakrabarty describes multiple plasmid containing Pseudomonas and the method for their preparation.

In the method of application Ser. No. 147,563 as in the method of the Cohen and Boyer patent, indirect selection of recombinant plasmids which are transformed into a recipient host is described. This method involves the selection for a marker in the transformed bacteria and the selection for the particular phenotypic trait. The selection method is laborious and time consuming in obtaining a particular phenotypic trait and provides one important reason why genetic research has been expensive. The reason for this result is that the transformation frequencies are low (or non-existent) in relation to a particular gene in a recombinant plasmid.

OBJECTS

It is therefore an object of the present invention to provide a method for rapidly and inexpensively obtaining a particular desired phenotypic trait in a transformed host. It is further an object to provide novel recombinant plasmid compositions as banks for obtaining the desired transformants. Finally it is an object of the present invention to provide novel, improved transformed hosts. These and other objects will become increasingly apparent by reference to the following description and the drawings.

IN THE DRAWINGS

FIGS. 1, 3, 4, 5 and 6 are electrophoresis gels showing various plasmid profiles. FIGS. 2 and 7 are physical maps of plasmids. In particular:

FIG. 1 is an agarose gel electrophoresis showing the origin and derivation of plasmids RP1, pRO1600, pRO1601, pRO1613 and pRO1614. DNA was prepared as described in Materials and Methods. A 25 μl sample of each DNA preparation was mixed with 10 μl of dye and subjected to electrophoresis. Samples were as follows: (A) PAO2(RP1)-11; (B) PAO2(RP1/pRO1600); (C) PAO2(pRO1601); (D) DNA from Escherichia coli V517, a multi-plasmid-containing strain used as a size standard (Macrina, F., D. Kepecko, K. Jones, D. Ayers and S. McCowen. Plasmid 14:7-420 (1978)); (E) PAO2 (pRO1613); (F) PAO2(pRO1614). Gels which contained 0.7 percent agarose were constructed and run as described previously (Hansen, J., and R. Olsen. J. Bacteriol. 135:227-238 (1978)).

FIG. 2 is a physical map of plasmids: (A) pRO1601, (B) pRO1613, (C) pRO1614, and (D) pRO1600. Numerical values in parentheses represent molecular size in daltons $\times 10^6$ for restriction enzyme cleavage fragments. These were determined using HindIII cleavage of phage lambda DNA and plasmid pBR322 DNA cleaved with combinations of two enzymes (double digest).

FIG. 3 is an agarose gel electrophoresis of plasmids formed with pRO1613 and cleaved with PstI. Samples were cleaved as described in materials and methods and run as described for FIG. 1. Samples were as follows: (A) pRO1613; (B) pRO1665, a lys-12 recombinant plasmid; (C) lambda cleaved with HindIII; (D) pRO1661, a met-28 recombinant plasmid.

FIG. 4 is an agarose gel electrophoresis of recombinant plasmids formed with pRO1614. Samples were cleaved with BamHI unless otherwise noted as described in materials and methods and run as described for FIG. 1. Samples were as follows: (A) pRO1655, a proA recombinant plasmid; (B) and (F) lambda cleaved with HindIII; (C) pRO1657, a proA recombinant plasmid; (D) pRO1614, the vector cleaved with HindIII; (E) pRO1658, a hisII recombinant plasmid; (G) pRO1615, an ilvB,C recombinant plasmid cleaved with HindIII.

FIG. 5 is an agarose gel electrophoresis of cleaved PAO chromosomal DNA. Samples were cleaved as described in materials and methods and run as described in FIG. 1. Samples were as follows: (A) un-cleaved DNA; (B) chromosome cleaved with HindIII; (C) chromosome cleaved with SalI; (D) lambda cleaved with HindIII; (E) chromosome cleaved with BamHI; (F) chromosome cleaved with PstI.

FIG. 6 is an agarose gel electrophoresis of recombinant plasmid gene-banks derived from the PAO chromosome. DNA for the pooled recombinant plasmids was prepared as described in the text. Samples in files F and J are the vector, pRO1614. Other files in the figure show plasmid DNA obtained from cultures inoculated from mixed suspensions which contained independently isolated recombinant plasmids as described in the specification.

FIG. 7 is a chromosomal map of PAO showing the map location of markers complemented by representative recombinant plasmids listed in Table 6. The map locations are those of Royle, Matsumoto and Holloway, J. Bacteriol. 145:145-155. Marker abbreviations are listed in footnote a of Table 1.

SUMMARY OF THE INVENTION

The present invention relates to an improvement in the gene splicing method wherein chromosomal DNA is partially and randomly cleaved into fragments with a restriction enzyme and spliced into a cleaved vector thereby joining the chromosomal DNA fragments to the vector to form a recombinant plasmid which comprises:

(a) mechanically fragmenting concentrated chromosomal DNA in the absence of bacterial cells into multiple fragments of randomly varying lengths; and (b) partially cleaving with a restriction enzyme and joining the mechanically fragmented and cleaved chromosomal DNA with the cleaved vector to form a bank of recombinant plasmids of varying sizes.

Further the present invention relates to a preserved recombinant plasmid bank adapted for transformation into a bacteria and then selection for particular recombinant plasmids, the bank containing multiple random length mechanically fragmented chromosomal DNA fragments having an average length between 0.1 and $20 \times 10^6$ daltons recombined with a vector and the plasmids being adapted for transformation into a bacterium having a particular mutant gene trait allowing for selection.

Finally the present invention relates to certain novel transformed hosts of the genus Pseudomonas into which the recombinant plasmids prepared by the method are transformed. The recombinant plasmids in a gene bank formed as a result of the initial fragmenting of the chromosomal DNA in the method of the present invention are highly transformable. Virtually any gene from the chromosomal DNA can be found in the collection of recombinant plasmids and can be selected using conventional selection techniques with plasmid free, auxotrophic bacteria for the transformation and defined media. The recombinant plasmids of the present invention are "closed" coiled or "super coiled" like a spring which promotes highly efficient transformation.

Because of the high, randomly sheared chromosomal transformation frequency, the selection can be made directly for almost any particular phenotypic or gene trait from the pool of super coiled DNA recombinant plasmids. This contrasts with the prior art method wherein indirect selection is made based upon a particular phenotypic marker in the chromosomal DNA usually an antibiotic marker or directed selection of rare closed circular DNA plasmids. The transformants in the prior art method are then tested for acquisition of a particular associated marker within the transformants along with the antibiotic marker, such as the ability to produce an essential amino acid. Many times the desired marker is not formed. In the method of the present invention the probability is great that the particular marker can be selected directly. The result is a considerable savings of time and money in obtaining desirable transformants.

A vortex mixer (such as a Vortex Genie ® Fisher Scientific Company) is preferably used to fragment the chromosomal DNA. An eccentric cup oscillates, causing a vortex in a test tube shaped container. The chromosomal DNA because of its length and relatively greater inertia with respect to the moving liquid breaks into relatively small fragments which have an average length between about 10 and $20 \times 10^6$ daltons. The fragmenting is accomplished essentially by whipping the long strands of chromosomal DNA.

DESCRIPTION OF SPECIFIC EMBODIMENTS

Figures 1, 2:
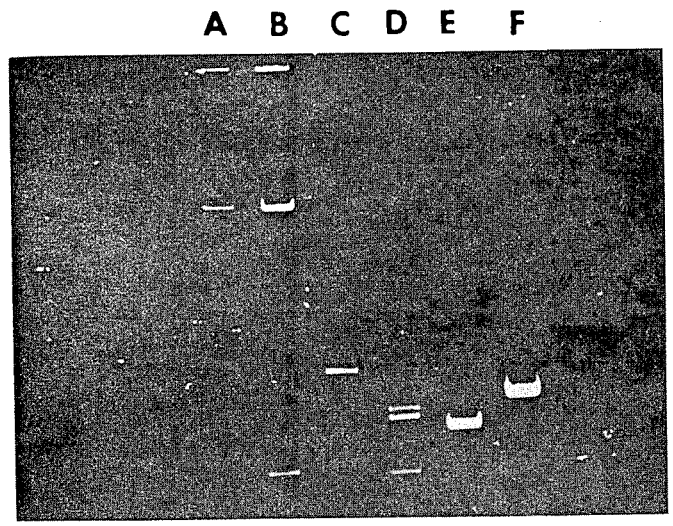

A host-vector system particularly for *Pseudomonas aeruginosa* PAO has been developed. Scattered regions of the strain PAO chromosome have been cloned by direct selection from a DNA gene-bank which contains over 1,000 independently isolated chromosome-vector recombinant plasmids. The use of partially digested chromosomal DNA facilitated the selection of a variety of strain PAO chromosomal markers.

As described in Ser. No. 147,563 the progenitor of the vector was a small, multi-copy plasmid, pRO1600, found in one PAO strain which had acquired RP1 in a mating experiment. The bacterial host range of vectors produced from pRO1600 resemble that for plasmid RP1. Two derivative-plasmids were formed; one, pRO1613, for cloning DNA cleaved with restriction endonuclease PstI. Another, pRO1614, was formed by deleting part of pRO1613 and fusion with plasmid pBR322. Plasmid pRO1614 utilizes cloning-sites within the tetracycline resistance region of pBR322.

Molecular cloning of chromosomal DNA using plasmids developed for that purpose has been reported for a variety of bacterial species. In most instances, the utility of the plasmid cloning-vector derives from the inactivation of an antibiotic resistance determinant of the vector as a consequence of the insertion of a piece of hetero-DNA from the chromosome into a site on the vector cleaved by a restriction endonuclease. Thus, the continuity of the vector gene and hence its expression is interrupted by insertion of foreign pieces of DNA. One of the most widely used plasmid vectors of this kind is plasmid pBR322 which has the advantage of a single restriction endonuclease site within its antibiotic resistance determinants for ampicillin resistance and tetracycline resistance (Bolivar, R, et al Gene 2:95-113.). However, the host range of pBR322 is limited to *Escherichia coli* and related bacterial strains prohibiting its usefulness in bacteria with disparate properties. Bagdasarian et al Developments in Genetics 1:411-422 (1979) and recently Wood et al J. Bacteriol. 145: 1488-1451 (1981) have reported the construction of a cloning vector for *Pseudomonas aeruginosa* to overcome this difficulty. Another plasmid vector has also been developed by Ditta et al which has been derived from the broad host range plasmid RK2 (Proc. Natl. Acad. Sci. USA 77:7347-7351). This system offers the advantage of potential for use in a wide variety of Gram negative bacterial species in view of its broad host range.

The present invention uses a preferred cloning vector system from a particular *Pseudomonas aeruginosa* strain which contains plasmid RP1. Plasmid RP1 is similar if not identical to RK2 used previously for this purpose and also plasmid RP4. One of the vectors, designated pRO1613 allows cloning of DNA previously digested with PstI using direct selection for the desired phenotype. Another vector, designated pRO1614, was derived from a deleted pRO1613 and the insertion of pBR322. Using these plasmids, we show cloning of widely scattered regions of the *Pseudomonas aeruginosa* strain PAO chromosome using a recombinant plasmid "gene bank" derived from the PAO chromosome. This gene bank has been used for the selection of a wide variety of recombinant plasmids which complement mutations in the chromosome of strain PAO.

MATERIALS AND METHODS

Bacterial strains and plasmids. The relevant properties of the bacterial strains and plasmids used in this study are listed in Table 1.

TABLE 1
Bacteria and plasmids

| | Genotype[a] | Reference or Source |
|---|---|---|
| Bacterial Strain | | |
| PAO1 | Prototroph | (1) |
| PAO2 | ser-3 | (1) |
| PAO25 | argF leu-10 | (1) |
| PAO236 | hisII ilvB,C lys-12 met-28 proA trpC,D,E, | (2) |
| PAO2003 | argH recA | (3) |
| PAO2178 | catAl met-9020 nar-9011 | (4)[b] |
| PAO2198 | arg-90310 catAl chu-9002 leu-9014 lys-9015 met-9020 nar-9011 trpA,B | b |
| PAO2324 | catAl met-9020 nar-9011 puuD6 tyu-9009 | b |
| PAO2369 | catAl cnu-9001 met-9020 nar-9011 puuE8 tyu-9025 | b |
| GMA052 | hisV | c |
| GMA057 | hisIV | c |
| GMA065 | hisIII | c |
| GMA253 | cys-5605 hisI | (1)[c] |
| *Pseudomonas putida* PPO131 | his-1 | d |
| *Pseudomonas fluorescens* PFO141 | his-1 | (5)[e] |
| *Escherichia coli* ED8654 | met $r_K^- m_K^-$ | f |
| *Klebsiella pneumoniae* KPM 100 | Prototroph | g |
| Plasmid | | |
| RP1 | Cb[r], Tc[r], PRR1[s], PRD1[s] | (6,7) |
| PBR322 | Cb[r], Tc[r] | (8) |
| pRO1600 | Cryptic | parent application |
| pRO1601 | pRO1600::TnI Cb[r] | parent application |
| pRO1613 | Cb[r] | parent application |
| pRO1614 | Cb[r], Tc[r] | parent application |

[a]Marker abbreviations: Bacterial Strains: arg, arginine; cat, catechol utilization; chu, choline utilization; cnu, carnosine utilization; cys, cysteine; his, histidine; ilv, isoleucine valine; leu, leucine; lys, lysine; met, methionine; nar, nitrate reductase; pro, proline; puu, purine utilization; rec, recombination; $r_K^- m_K^-$, *Escherichia coli* K12 restriction and modification; ser, serine; tryp, tryptophan; tyu, tyrosine utilization. Plasmids: Cb[r], carbenicillin resistance; Tc[r], tetracycline resistance; Km[r], kanamycin resistance; PRR1[s], sensitive to phage PRR1; PRDL[s], sensitive to phage PRD1.
[b]Matsumoto, H. et al. Mol, Gen. Genet. 167:165-176 (1978).
[c]Mee, B., and B. Lee. Genetics 62:637-696 (1969).
[d]Mutant of ATCC 12633.
[e]Mutant of strain PFO14 isolated from milk and received from J. Jezeski, University of Minnesota.
[f]Strain K12, received from D. Jackson.
[g]Stock culture, Department of Microbiology and Immunology, University of Michigan Medical School.
(1) Royle, P., H. Matsumoto, and B. Holloway. J. Bacteriol. 145:145-155 (1981).
(2) Haas, D., and B. Holloway. Mol. Gen. Genet. 144:243-251 (1976).
(3) Chandler, P., and V. Krishnapillai. Mutat. Res. 23:15-23 (1974).
(4) Royle, P., H. Matsumoto, and B. Holloway. J. Bacteriol. 145:145-155 (1981).
(5) Olsen, R., E. Metcalf, and J. Todd. J. Virol. 2:357-364 (1968).
(6) Olsen, R., and P. Shipley. J. Bacteriol. 113:772-780 (1973).
(7) Olsen, R., J. Siak, and R. Gray. J. Virol. 14:689-699 (1974).
(8) Bolivar, R., R. Rodriguez, P. Greene, M. Betlach, H. Heyneker, H. Boyer, J. Crosa, and S. Falkow. Gene 2:95-113 (1977).

Media. Minimal medium (VBG) and complex medium (TN) were prepared as described in Olsen, R., and P. Shipley. J. Bacteriol. 113:772-780 (1973). When nutritional selection for transformants was done, amino acid requirements were satisfied by the addition of these components to a final concentration of 5 mM. Antibiotic supplements were as described in the tables. Selection or indirect testing for the acquisition of catabolic markers was done using a minimal medium (MMO) described previously for this purpose (Stanier, R., N. Palleroni, and M. Doudoroff, J. Gen. Microbiol. 43:159-271 (1966)). Carbon sources were incorporated into MMO at a final concentration of 0.2 percent.

Preparation of DNA. Plasmid DNA was prepared using a modification of the method of Guerry, LeBlanc and Falkow, J. Bacteriol. 116:1064-1066 (1973). Cells were grown overnight on the surface of TN-agar medium plates. In some cases, carbenicillin (Cb, 0.5 mg per ml) was included in the medium to maintain selection for plasmids. The cells were harvested from the surface of the plates by adding 5 ml sterile water to each plate and scraping with a glass rod. These suspensions were decanted and pooled into a bottle which was shaken vigorously to disperse clumps of cells. The cell suspension was then centrifuged at ambient temperature and the pellets suspended in TS buffer (9% sucrose—0.05 M Tris, pH 8) (10 ml buffer for each centrifuge tube with about $1.5 \times 10^{10}$ cells). The following additions and manipulations were then done with each suspension: Na₂EDTA (0.5 M, pH 8.0) which functions as a chelating agent for metal ions was added to a final concentration of 0.08 M. This was followed immediately by the addition of lysozyme (10 mg per ml in 0.25 M tris, pH 8.0) to a final concentration of 0.77 mg per ml. The tubes were then briefly mixed on a vortex mixer (Vortex Genie ® Fisher Scientific Company) and incubated at 37° C. for 5 min. Following this, sodium dodecyl sulfate (SDS, 15 percent in distilled water) was added to a final concentration of 2 percent. The tubes were inverted slowly several times to mix and then incubated in a water bath for 5 min at 37° C. During this time they were removed several times and slowly inverted to promote lysis of the cells. Finally, 5 M NaCl in distilled water was added to a final concentration of 0.95 M and mixed into the suspension by several gentle inversions. The tubes were then placed into an ice-water bath for 10 min followed by storage overnight at 4° C. Precipitation of chromosome, harvest of plasmid DNA and CsCl-ethidium bromide centrifugation was then done as described previously by Hansen and Olsen, J. Bacteriol. 135:227-238 (1978). DNA was stored frozen in TO buffer (Tris 10 mM-1 mM Na₂ EDTA, pH 8) and thawed slowly in ice water when used.

Recombinant plasmids were surveyed for their size using cells harvested from a path of growth on selective medium and lysis of cells by the procedure of Hansen and Olsen.

Chromosomal DNA was harvested from *Pseudomonas aeruginosa* strain PAO1 which had been selected for resistance to rifampin (50 μg per ml) in the laboratory. The procedure described above (modification of Guerry et al.) was used for chromosomal DNA too except that the lysed cell suspensions were given two 30 sec pulses at full speed on a vortex mixer prior to the addition of 5 M NaCl. This was done to fragment the chromosome. These lysed suspensions were then salt-precipitated followed by DNA precipitation and CsCl-ethidium bromide centrifugation as described previously for plasmid DNA.

Transformation. Pseudomonads were transformed using a modification of the method of Mercer and Loutit, J. Bacteriol. 140:37-42 (1979). Bacteria were grown overnight on TN agar and a portion then inoculated into TN broth with incubation for 2 to 3 hours reaching a cell density of $1 \times 10^8$ per ml. The cells were centrifuged at 4° C. and the pellet suspended in one-half volume cold sterile MgCl₂ (0.15 M in distilled water). The pellet was dispersed and held in an ice-water bath for an additional 5 min. The cells were centrifuged and the pellet suspended as before but then held in the ice-water bath for 20 min. The cells were centrifuged again and the pellet suspended in one-tenth volume cold MgCl$_2$ (0.15 M). Transforming-DNA (10 to 50 μl) was placed in a cold centrifuge tube and 0.2 ml of the above cells added with mixing. This mixture was incubated in an ice-water bath for 60 min followed by a heat-pulse in a water bath at 37° C. for 3 min while gently swirling the tube. The DNA-cell mixture was then placed immediately in an ice-water bath and incubated for 5 min. After this, 0.5 ml TN broth was added and the suspension incubated at 37° C. for 1 to 2.5 hours. The cells were then plated on selective medium and the plates were incubated at appropriate temperatures for 48 hours.

*Escherichia coli* and *Klebsiella pneumoniae* were transformed using a modification of the method of Davis, Botstein and Roth, In Advanced Bacterial Genetics: a manual for genetic engineering. Cold Spring Harbor Laboratory, Cold Spring Harbor (1980 pp 134–137). For this, bacteria were grown as above and cultures chilled at the end of the growth period in an ice-water bath for 10 min. The cells were then centrifuged at 4° C. and pellets were suspended in one-half volume CTG buffer (CaCl$_2$, 50 mM; glycerol, 10 percent; thymidine, 50 μg per ml). The cells were dispersed and incubated 5 min in a bath at 0° C. They were then centrifuged and pellets were suspended at one-twentieth volume of the original culture. 0.2 ml cells were added to tubes which contained 20 to 100 μl DNA and mixed; these were held 3 min in an ice-water bath. The tubes were then transferred to a 45° C. water bath and slowly swirled for 2 min; they were then placed in an ice-water bath for 5 min. Following this, 0.5 ml of TN broth was added and the mixture was incubated at 37° C. for 0.5–2.5 hours. Samples of these transformation mixtures were then plated at 37° C. on selective medium. For both transformation procedures, all materials, including pipettes were at 4° C. unless otherwise noted.

Enzymes. Restriction endonuclease (Bethesda Research Laboratories, Rockville, Md.) digestion and ligation were done as is shown in the prior art. Digested DNA to be ligated was incubated for 20 hours at 17° C. Ligations were done in a volume of 20 μl or less. In some experiments, this required concentration of cleaved DNA by ethanol precipitation prior to the addition of ligase and buffer. These ligation mixtures were used for transformation as described above and in the Tables.

Development of a cloning-vector system. Over the years, the inventor has routinely transferred plasmid RP1 from one bacterium to another and, on some occasions, examined the transconjugants for the acquisition of a plasmid whose size and phenotypic characteristics correspond to that of the donor bacterium which contains RP1. On one such occasion, following the preparation of plasmid DNA from the recipient, it was noted the presence of two plasmids; one corresponding to RP1 and another smaller plasmid of approximately 2 Mdaltons in molecular size. The recipient bacterium used for these experiments never before has been shown to contain such a small plasmid so this result suggests the rare occurrence and fortuitous observation of a RP1 mutation which occurred during transfer to a recipient. This is the invention described in application Ser. No. 147,563. The relationship of these plasmids is shown in FIG. 1. In FIG. 1, file A is shown RP1 plasmid DNA isolated from a PAO2(RP1) transconjugant. In file B, DNA from another PAO2(RP1) transconjugant used for the preparation of plasmid DNA showed two plasmids; RP1 at the top of the gel and a smaller plasmid near the bottom which we have designated pRO1600. Its size was 2 Mdaltons in relation to plasmid DNA standards prepared from *Escherichia coli* V517 (Macrina, F., D. Kepecko, K. Jones, D. Ayers, and S. McCowen, Plasmid 14: 7-420 (1978) shown in file D. We used the DNA preparations shown in files A or B to transform PAO25 with selection for the acquisition of either carbenicillin (Cb$^r$), tetracycline (Tc$^r$) or kanamycin (Km$^r$) resistances. The rationale here was that one of these determinants from RP1 might be included within pRO1600, or alternatively, a derivative might be obtained of the small plasmid designated pRO1600 which had acquired Tnl, a Cb$^r$ transposon, from RP1 in the mixed DNA. The results of this are shown in Table 2. As can be seen from Table 2, no transformants with only Tnl were obtained from PAO2(RP1)-11 DNA whereas 8 percent were Cb$^r$ only of those which obtained when PAO2 (RP1/pRO1600) DNA was used to transform. One such transformant is shown in FIG. 1, file C. It was designated pRO1601 and its size is about 5.2 Mdaltons. This result was consistent with the acquisition of Tnl (3.2 Mdaltons) by pRO1600 (2 Mdaltons). Plasmid pRO1601 and other similar Tnl-transposed transformants which were only Cb$^r$ derived from the experiment shown in Table 2 were used to prepare plasmid DNA and were cleaved by PstI or BglI restriction endonucleases and the fragments were subjected to agarose gel electrophoresis.

TABLE 2

Selection of pRO1600:Tnl plasmids[a]

| Source of Transforming DNA[b] | Number of Transformants | Percent nonselected markers acquired by transformants | |
|---|---|---|---|
| | | Tc$^r$ | Km$^r$ |
| *P. aeruginosa* PAO2 (RP1)-11 | 190 | 100 | 100 |
| *P. aeruginosa* PAO2 (RP1/pRO1600) | 397 | 92 | 92 |

[a]Approximately 0.5 μg of either plasmid DNA preparation was used for transformation as described in materials and methods. Strain PAO2 was used as the recipient. Selection for transformants resistant to Cb was on TN agar medium with 0.5 mg of carbenicillin per ml. Cb$^r$ transformants were picked onto TN agar medium with Tc (60 μg per ml) or VBG with serine and Km (60 μg per ml).
[b]These strains were transconjugants derived from mating PAO25(RP1) × PAO2 and selecting for the acquisition of Cb$^r$.

Partial digests were also done to determine contiguity of the fragments. The results of one of these determinations are shown in FIG. 2, panel A. Since the digest pattern for Tnl was known from previous work, the map of pRO1600 shown in FIG. 2, panel D was deduced. Similar determinations on eleven other Cb$^r$ transformants yielded different regions of pRO1600 altered as a consequence of a Tnl insertion. However, none showed a Tnl insertion within the 0.83 Mdalton BglI fragment. Therefore, the results of this survey suggest that this 0.83 Mdalton region includes the replication functions for plasmid pRO1600. Perhaps then, other regions of pRO1600 may be dispensible and either the size of pRO1601 may be reduced by PstI digestion and ligation of the replication region to the fragment with Cb$^r$, or that the replication region could be added to plasmid pBR322, which is non-viable in PAO to provide replication functions in Pseudomonas. Accordingly, pRO1601 was digested with PstI and a portion of this digest was added to pBR322 digested with PstI and the mixture was ligated. These preparations (with and without pBR322) were then used to transform PAO2 and the results of this are shown in Table 3.

TABLE 3

Derivation of cloning plasmids[a]

| Plasmid DNA used | Treatment of DNA | Number of transformants[b] | Antibiotic resistance |
|---|---|---|---|
| pBR322 | (none) | 0 | Cb[r] |
| pRO1601 | (none) | 69,000 | Cb[r] |
| pRO1601 | PstI cleavage + ligation | 70 | Cb[r] |
| pRO1601 + pBR322 | PstI cleavage + ligation | 2<br>4 | Cb[r]<br>Cb[r], Tc[r] |

[a]About 0.5 μg of plasmid DNA was treated as described in the Table and transformed into PAO2 as described in materials and methods.
[b]Selection was as described in Table 2.

Undigested pRO1601 and pBR322 were also used as controls in this experiment. Several transformants from the PstI-digested pRO1601 and the mixture of pRO1601 plus pBR322 were purified and DNA was prepared and analyzed by restriction endonuclease cleavage as before. The results of this are shown in FIG. 2, panels B and C. In the former case, a plasmid designated pRO1613 which contains only two PstI sites was obtained. In the latter case, a plasmid designated pRO1614 which contained only a portion of pRO1601 and all of pBR322 was obtained. In the latter instance, apparently part of the beta-lactamase gene of TnI, known to have a PstI site within it (Bolivar, R., et al, Gene 2:95-113 (1977)), has matched up with an analogous contiguous region of pBR322 to reconstitute a viable beta-lactamase determinant.

I next determined the bacterial host range of pRO1613 or pRO1614 derived from the experiments shown in Table 3. For this, I used several bacterial strains of disparate physiological properties. The choice of either pRO1613 or pRO1614 for this was influenced by the intrinsic Cb[r] or Tc[r] of these strains which would allow unambiguous scoring of transformants for their acquisition of the antibiotic resistances encoded by the plasmids. The data resulting from this preliminary host range determination are shown in Table 4.

TABLE 4

Host range of cloning plasmids pRO1613 and pRO1614[a]

| Plasmid DNA[b] | Recipient bacteria | Selection[c] | Number of transformants per μg DNA |
|---|---|---|---|
| pRO1613 | P. aeruginosa PAO2 | Cb[r] | 132,000 |
| pRO1614 | P. aeruginosa PAO2 | Tc[r] | 38,000 |
| pRO1614 | P. putida PP0131 | Tc[r] | 960 |
| pRO1614 | P. fluorescens PF0141 | Tc[r] | 24,000 |
| pRO1614 | E. coli ED8654 | Tc[r] | 5,500 |
| pRO1614 | K. pneumoniae KPM100 | Tc[r] | 1,300 |

[a]Escherichia coli and Klebsiella pneumoniae were transformed using the CTG procedure described in materials and methods. Pseudomonas strains were transformed using the Mercer and Loutit procedure.
[b]DNA was prepared from PAO2 which contained either pRO1613 or pRO1614.
[c]Selection was as described in Table 2. Pseudomonas putida or Pseudomonas fluorescens were incubated at 25° C. Other strains were at 37° C.

The data in the Table indicate the broad host range of the plasmids among pseudomonads, E. coli and Klebsiella. Perhaps this list will be extended as transformation procedures are developed for other gram-negative bacterial species of interest for molecular cloning. Although the same DNA preparation for pRO1613 or pRO1614 was used in all cases here, the number of transformants obtained varied with the recipient. This may reflect restriction of the plasmids in view of its preparation from strain PAO and perhaps the use of sub-optimal transformation procedures for the bacterial strains shown here.

Figure 3:
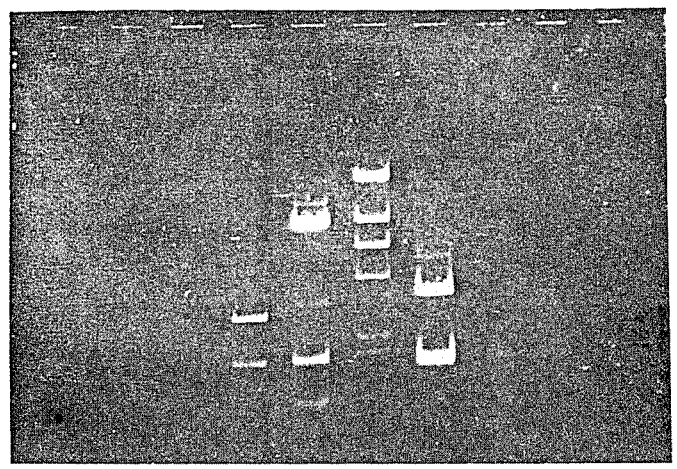
Figure 4:
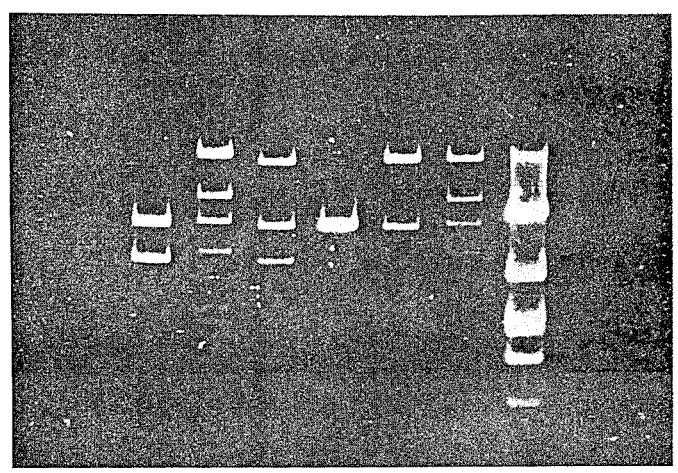

Cloning the PAO chromosome. I tested the utility of pRO1613 and pRO1614 for cloning using PstI-cleaved pRO1613 and PstI-cleaved PAO chromosome. Similarly, pRO1614 and chromosome were cleaved with EcoRI, HindIII, BamHI or SalI. The DNA suspensions were mixed after cleavage, ligated and transformed into PAO236. Strain PAO236 is a multiple auxotroph and transformants were selected for their nutritional independence. Usually, one or two nutritionally independent transformants were obtained this way from an experiment and these were purified, characterized for antibiotic resistance, and used to prepare plasmid DNA for analysis. Plasmid DNA for typical transformants was cleaved with the enzyme used for their preparation and the electropheregrams for some of these digests are shown in FIGS. 3 and 4. File A, FIG. 3 shows a PstI digest of the vector, pRO1613. The upper band is the PstI fragment internal to part of TnI which was retained by pRO1613 when pRO1601 was reduced in size. This piece is lost during PstI digestion and cloning of PstI-cleaved hetero-DNA and therefore is absent in digests of recombinant plasmids shown in files B and D. File B shows a recombinant plasmid designated pRO1665 which complements the lys-12 mutation in PAO236; file D is a recombinant plasmid designated pRO1661 which complements the met-28 mutation in this strain. In addition to the replicator region (lower band, file A) of pRO1613, file B shows two bands derived from chromosomal cloning. It is uncertain whether these two bands were derived from a partially digested contiguous region of the chromosome or whether they represent the random association of two different fragments during the cloning process. File D, on the other hand shows a single fragment associated with the met-28+ phenotype of this recombinant plasmid. To further confirm the authenticity of these recombinant plasmids, plasmid DNA was extracted from the strains shown in FIG. 3 and used to re-transform PAO236. As expected, a high frequency of transformation, corresponding to that observed for pRO1613 using Cb[r] selection, occurred, using direct selection for nutritional independence with the recombinant met-28+ or lys-12+ plasmids.

When pRO1614 was used as the vector-plasmid, transformants with markers corresponding to PAO236 were isolated using HindIII or BamHI. However, no transformants were obtained for plasmid and chromosome DNA cleaved with EcoRI or SalI. FIG. 4 shows transformant-DNA cleaved with HindIII or BamHI for several of the recombinant plasmids made using these enzymes. File D shows the vector, pRO1614, cleaved at a single site as expected. A similar band is observed for files A, C, E, and G which contain recombinant plasmids complementing respectively proA, proA, hisII and ilvB,C mutations of PAO236. The ilvB,C+ recombinant plasmid was produced using HindIII; the others were made using BamHI. The plasmids shown in files A and C are another example of varied sizes obtained for a given selection. The lower band is common to both and likely encodes for proA. The upper band in file C, then, is either a randomly associated fragment derived from another region of the chromosome or is the result of chromosomal DNA partially digested with BamHI. Table 5 summarizes the composition of recombinant plasmids shown in FIGS. 3 and 4.

TABLE 5
Composition of PAO recombinant plasmids.

| Recombinant Plasmid Designation | PAO236 Marker | Enzyme Used | Fragment sizes ($\times 10^6$ daltons)[a] |
|---|---|---|---|
| pRO1613 | (vector) | PstI | 1.8, 1.1 |
| pRO1665 | lys-12 | PstI | 6.1, 1.1, 0.74 |
| pRO1661 | met-28 | PstI | 2.4, 1.1 |
| pRO1614 | (vector) | BamHI | 3.9 |
| pRO1655 | proA | BamHI | 3.9, 2.3 |
| pRO1657 | proA | BamHI | 12.1, 3.9, 2.4 |
| pRO1658 | hisII | BamHI | 13.6, 3.9, 0.82 |
| pRO1615 | ilvB,C | HindIII | 3.9, 1.8, 1.1, 0.95, 0.74, 0.50 |

[a]Fragment sizes were calculated from data shown in FIGS. 3 and 4.

The sum of the fragment sizes for pRO1658 is about 18.3 Mdaltons representing 14.4 Mdaltons of the PAO chromosome. Recombinant plasmids of this size are near the upper limit of those obtained to date using direct selection for the acquisition of nutritional markers. Not all the recombinant plasmids described here are stable in the absence of nutritional and antibiotic selection in appropriate mutant bacteria. For example, pRO1615 requires both selection for ilvB,C+ and Cb$^r$ for maintenance in PAO236. If Cb$^r$ selection is omitted, a nutritionally independent chromosomal recombinant occurs; if ilvB,C selection is omitted, a deleted version of pRO1615 occurs (data not shown). However, the other plasmids described in Table 5, and for the most part all others obtained to date, are stable in recA+ PAO bacteria in the absence of nutritional or antibiotic selection on TN agar maintenance medium.

Figure 5:
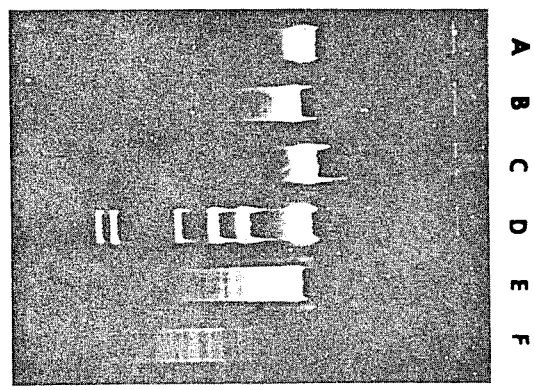

Derivation of a chromosomal gene bank for PAO. Over a period of years, the number of recombinant plasmids obtained using direct selection and the enzymes described in the foregoing work was small in comparison to the total yield of transformants obtained using antibiotic-selection. When these transformants selected for antibiotic resistance were scored for insertional inactivation of an antibiotic resistance marker resulting from the addition of chromosomal DNA, few were found. Therefore, the cloning efficiency was low. Two bases for this may be relevant: the donor chromosomal DNA may be poorly cleaved by the enzymes used and/or the use of recA+ transforming-recipient bacteria may diminish the recovery of recombinant plasmids. I investigated the former possibility by digesting PAO chromosomal DNA with the enzymes used in the foregoing work and the results of this are shown in FIG. 5. These digests show variable cleavage of the fragmented chromosomal DNA preparation (described in Materials and Methods).

On the basis of the result shown in FIG. 5, file E I prepared a BamHI digest of fragmented DNA from PAO to be used in evaluating a possible enhancement of PAO which is recA (Chandler, P., and V. Krishnapillai. Mutat. Res. 23:15–23(1974)). For this I also cleaved pRO1614 with BamHI and selected PAO2003 transformants for their acquisition of Cb$^r$. These Cb$^r$ transformants were then streaked onto medium which contained Tc to determine insertional inactivation of the Tc$^r$ region of the vector as a consequence of the inclusion of a chromosomal fragment at its BamHI cleavage site. When this was done, 132 of 552 colonies picked were Tc$^s$ (24 percent). In other experiment, where DNA from PAO was prepared from a rifampin resistant mutant (50 μg/ml), 958 of 3090 transformant colonies picked were Tc$^s$ (31 percent). Therefore, these data support the utility of recA strain (PAO2003) for cloning in *Pseudomonas aeruginosa* as suggested previously by Carbon et al for cloning in *Escherichia coli* (Carbon, J. et al, Recombinant molecules: impact on science and society. Raven Press, New York (1977)). In the second set of experiments described above, I also did direct selection for the acquisition of rifampin resistance or an argH+ recombinant plasmid complementing the argH mutation in the chromosome of PAO2003. Two recombinant plasmids of different size were found for rifampin resistance; one argH+ recombinant plasmid was observed. As in all previous examples of recombinant plasmids discussed here, DNA from PAO2003 transformants containing these plasmids was used to retransform PAO2003 and the relevant markers were acquired at a high frequency independent of selection for either Cb$^r$ or the selective marker. Therefore, these were authentic recombinant plasmids for the markers relevant to their initial selection.

Figure 6:
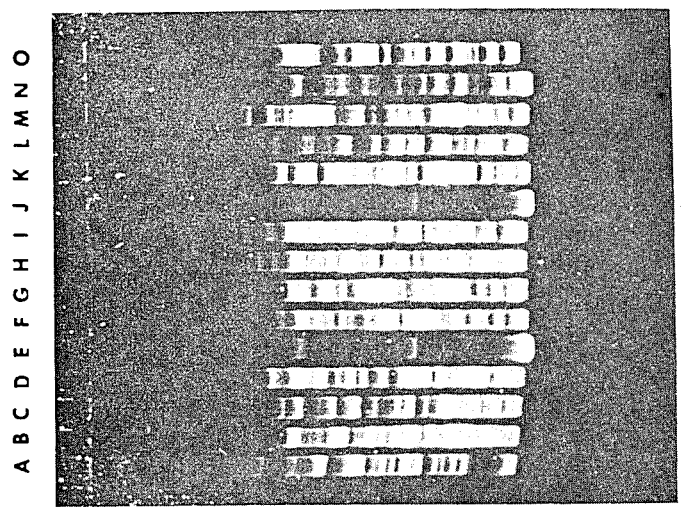

Forty-four of the 132 Tc$^s$ transformants from the first experiment described above were patched onto each of 3 TN agar plates which contained Cb (0.5 mg/ml) and 100 Tc$^s$ clones per agar plate from the 938 obtained in the second experiment described above were patched on the same media. Following overnight incubation, the cells were washed from each agar plate and 0.5 ml used to inoculate 10 nutrient agar plates which contained Cb. These ten TN agar plates (per inoculum source) were harvested and extracted for plasmid DNA which was subsequently centrifuged in CsCl ethidium bromide gradients. The plasmid DNA band was harvested from the gradient and electrophoresed to determine their content of recombinant plasmids resulting from the inocula derived from mixed-suspensions of transformants. These are shown in FIG. 6. In FIG. 6, files A, B and C are shown plasmid DNA preparations derived from a mixed culture resulting from the inoculum which contained 44 independently isolated pRO1614 Tc$^s$ transformants. The other mixed culture DNA preparations were derived from inocula prepared from 100 Tc$^s$ transformant colonies. None of the files show unique plasmids corresponding to the number of transformants used for their preparation. However, throughout the files, some plasmid bands are more prominent than others perhaps indicative of either higher copy number recombinant plasmids at those locations or alternatively, several different recombinant plasmids of approximately the same size. I favor the second alternative in view of the utility of these plasmid DNA gene banks for selecting almost any marker tested to date when various mutants are used as transforming-recipient bacteria. Also, when these DNA gene banks are used as a source of transforming DNA with direct selection for a given marker, the frequency of transformation varies widely for various markers. This suggests that some recombinant plasmids may be present in low concentration and not visualized on the agarose gel shown in FIG. 6.

A summary of the recombinant-plasmid phenotypes isolated from the earlier work with direct selection and also from the gene banks shown in FIG. 6 is presented in Table 6.

TABLE 6
Representative recombinant plasmids of the PAO chromosome[a]

| PAO strain and plasmid designation | Markers complemented |
|---|---|
| PAO25 (pRO1703) | argF |
| PAO236 (pRO1615)[b] | ilvB,C |
| PAO236 (pRO1616)[b] | met-28 |
| PAO236 (pRO1654)[b] | lys-12 |
| PAO236 (pRO1657)[b] | proA |
| PAO236 (pRO1658)[b] | hisII |
| PAO2003 (pRO1700)[b] | rifA |
| PAO2003 (pRO1702)[b] | argH |
| PAO2178 (pRO1669)[b] | catA met-9011 |
| PAO2198 (pRO1687) | chu-9002 |
| PAO2198 (pRO1689) | lys-9015 |
| PAO2198 (pRO1690) | chu-9002 trpA,B |
| PAO2198 (pRO1694) | leu-10 |
| PAO2324 (pRO1677) | puuD |
| PAO2324 (pRO1683) | met-9011 |
| PAO2369 (pRO1679) | nar-9011 |
| PAO2369 (pRO1680) | nar-9011 tyu-9009 |
| PAO2369 (pRO1682) | catA |
| GMA052 (pRO1707) | hisIV |
| GMA057 (pRO1705) | hisV |
| GMA065 (pRO1713) | hisIII |
| GMA253 (pRO1704) | hisI |

[a] The derivation of the mixed-plasmid DNA suspensions is discussed in the text.
[b] These recombinant plasmids were obtained using appropriate PAO nutritional mutants. They were isolated using direct selection from cleaved chromosome and vector DNA that was ligated.

In Table 6, only one recombinant plasmid for each phenotype is listed. However, in most instances, several recombinant plasmids for a given phenotype were isolated and they vary in size for their independent isolations; the larger versions show more than one BamHI cleavage site when plasmid DNA is isolated and digested from the various isolates of the same phenotype. As shown earlier in FIG. 4, however, a band unique to the marker in question is found in all recombinant plasmids of the same phenotype. In some cases, selection for one marker results in the isolation of recombinant plasmids which also include adjacent markers. For example, plasmids pRO1680, pRO1669 and pRO1690 which respectively were selected for nar-9011, met-9011, and trpA,B were subsequently tested for adjacent markers shown on the Royle et al. map (Royle, P., H. Matsumoto, and B. Holloway. J. Gen. Microbiol. 43:159-271 (1981)) and were found to complement these too. On the other hand, recombinant plasmids have been selected which encode for these markers singly. These results suggest that the conditions used for digestion of chromosomal DNA result in incomplete digestion of the chromosome allowing for the isolation of fragments of variable length from the same region of the chromosome.

Figure 7:
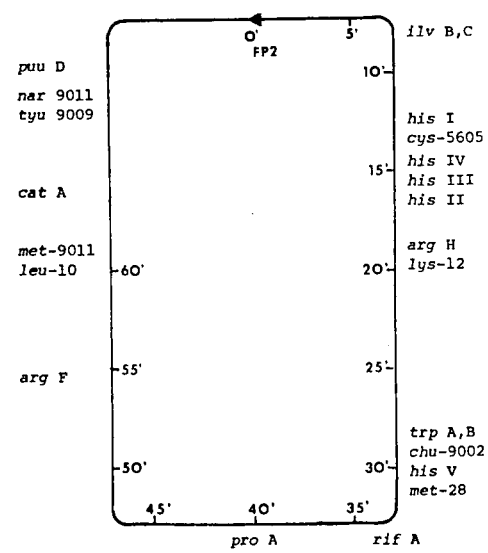

The recombinant plasmids listed in Table 6 correspond to scattered regions of the PAO chromosome. This is evident from FIG. 7 where their map location corresponding to chromosomal mutations they complement is shown. For this, I have used the most recent map of Royle et al as a guide to position the markers in relation to a time of entry map using PAO sex factors and transductional analysis linkage determinations. Most of the plasmids listed in Table 6 and FIG. 7 were obtained from the gene pools shown in FIG. 6. This result suggests that procedures for the preparation of chromosome, cleavage with BamHI and indirect selection for the isolation of recombinant plasmids followed by the preparation of recombinant DNA from mixed cultures is suitable as a general protocol. These procedures apparently do not bias against the molecular cloning of significantly extensive regions of the PAO chromosome.

Clarke and Carbon sheared the *Escherichia coli* chromosome and then formed hybrid plasmids in vitro using poly(dA.dT) "connectors" (Clarke, L., and J. Carbon. Proc. Nat. Acad. Sci. USA 72:4361-4365 (1975)). This was done to diminish the likelihood of recovering chromosomal fragments which contained cleavage sites in structural genes and to obviate the need in the vector for a cloning site which would be insertionally inactivated with the addition of a cloned fragment of chromosome. In the present invention the recovery of DNA fragments cleaved in structural genes was minimized by the method of the present invention which reproducibly results in partially digested chromosomal DNA. The utility of this is suggested by the isolation of recombinant plasmids with additional BamHI sites within the BamHI-cloned DNA. Therefore, if a particular allele contained a cleavage site within its structure, partial digests enhanced the recovery of an intact allele. In this regard, the map distribution (FIG. 6) of recombinant plasmids listed in Table 6 suggests that partially cleaved fragments of chromosomal DNA were isolated from disparate regions of the PAO chromosome. Furthermore, the use of BamHI for this purpose may have promoted the recovery of diverse recombinant plasmids in view of the extent of cleavage of this enzyme of the chromosome and the distribution of BamHI cleavage sites on the chromosome.

The following table shows the recombinant plasmids from application Ser. No. 147,563 and the numbers assigned by the Northern Regional Research Laboratory in Peoria, Ill.

| Plasmid | NRRL No. |
|---|---|
| RP1 | B-12123 |
| pRO/RP1/1600 | B-12124 |
| pRO1601 | B-12125 |
| pRO1613 | B-12126 |
| pRO1614 | B-12127 |
| pRO1615 | B-12149 |
| pRO1616 | B-12148 |

I claim:

1. In a gene splicing method wherein chromosomal DNA is partially and randomly cleaved into fragments with a restriction enzyme and spliced into a cleaved vector thereby joining the chromosomal DNA fragments to the vector to form a recombinant plasmid, the improvement which comprises:
   (a) mechanically fragmenting concentrated chromosomal DNA in the absence of bacterial cells into multiple fragments of randomly varying lengths, wherein the average length of the fragments is between 0.1 and $20 \times 10^6$ daltons;
   (b) partially cleaving with a restriction enzyme the mechanically fragmented and cleaved chromosomal DNA; and
   (c) joining the endonuclease cleaved mechanically fragmented DNA with an endonuclease cleaved vector selected from derivatives of pRO1600 as carried in NRRL-B-12124 to form a bank of recombinant plasmids of varying sizes, wherein the bank contains intact alleles which are usually cleaved by the restriction endonuclease.

2. The method of claim 1 wherein the vector is plasmid PRO1601, 1613, 1614 as carried in NRRL-B-12125, 12126 and 12127 respectively as the pRO1600 derivative.

3. The method of claim 1 wherein the chromosomal DNA is harvested from a Pseudomonas.

4. The method of claim 3 wherein the chromosomal DNA is harvested from *Pseudomonas aeruginosa*.

5. The method of claim 1 wherein the restriction enzyme is an endonuclease selected from BamHI, HindIII, SalI, PstI, and BglII.

6. The method of claim 1 wherein the mechanical fragmenting is accomplished using a vortex mixer.

7. The method of claim 1 wherein the chromosomal DNA is cleaved into segments having an average length of between about 10 and $20 \times 10^6$ daltons.

8. The method of claim 1 wherein the fragmenting is accomplished by whipping the chromosomal DNA fragments.

9. The method of claim 1 wherein the fragmenting is accomplished in the presence of lysozyme, detergent and a chelating agent.

10. The method of claim 1 wherein the recombinant plasmids are transformed into a receptive microorganism and wherein selection is made for a particular useful gene trait present in the chromosomal DNA.

11. A preserved recombinant plasmid bank adapted for transformation into bacteria and then selection for particular recombinant plasmids, the bank containing multiple random length mechanically fragmented chromosomal DNA fragments having an average length between 0.1 and $20 \times 10^6$ daltons which have been partially cleaved with a restriction enzyme and then recombined with a vector selected from derivatives of pRO1600 as carried in NRRL-B-12124 and the plasmids being adapted for transformation into a bacterium having a particular mutant gene trait allowing for selection wherein the bank contains intact alleles which are usually cleaved by the restriction endonuclease.

12. The recombinant plasmid of claim 11 wherein the bank is a concentrate containing at least about 100 different recombinant plasmids in admixture.

13. The recombinant plasmid of claim 11 wherein the bank is preserved by being frozen in the presence of a freezing stabilizing agent.

14. The recombinant plasmid of claim 13 wherein the freezing stabilizing agent is a 2-amino-2-hydroxymethyl-1, 3-propanediol and disodium ethylene diamine tetracetic acid mixture with a pH of about 8.

15 A bacterial strain containing various recombinant plasmids prepared by the method of claim 1.

16. A bacterial strain containing various recombinant plasmids prepared by the method of claim 1, wherein the vector is selected from pRO1600, 1613 and 1614 as carried in NRRL-B-12125, 12126 and 12127, respectively as derivatives of pRO1600.

* * * * *